US00PP09441P

United States Patent [19]

VandenBerg

[11] Patent Number: Plant 9,441

[45] Date of Patent: Jan. 23, 1996

[54] CHRYSANTHEMUM PLANT NAMED 'WHITE BLUSH'

[75] Inventor: Cornelis P. VandenBerg, Salinas, Calif.

[73] Assignee: Yoder Brothers, Inc., Barberton, Ohio

[21] Appl. No.: 296,467

[22] Filed: Aug. 26, 1994

[51] Int. Cl.[6] ..... A01H 5/00

[52] U.S. Cl. ..... Plt./82.1

[58] Field of Search ..... Plt./78, 77, 82.1, Plt./82.2

[56] References Cited

U.S. PATENT DOCUMENTS 4,616,099 10/1986 Sparkes ..... 47/58

OTHER PUBLICATIONS

Broertjes, et al., 1980, "A mutant of a mutant of a . . . irradiation of progressive radiation–induced mutants in a mutation breeding programme with *C. morifolium*", Euphytica, 29:525–530.

Gosling, ed., 1979 "The Chrysanthemum Manual–6th edition", The National Chrysanthemum Society, London, Essex Telefraph Press, LTD, London, pp. 329–336.

Broertjes, et al., 1978, "Applicaiton of Mutation Breeding Methods in the Improvement of Vegetatively Propagated Crops", Elsevier Sci. Pub. Co., New York, pp. 162–175.

Searle, et al., 1968, "Chrysanthemums the Year Round–3rd edition", Blanford Press, London, pp. 27–29, 320–327.

Chan, 1966,. "Chrysanthemum and rose mutations induced by X–rays", Am. Soc. Hort. Sci., vol. 88, pp. 613–620.

Broertjes, 1966, "Mutation breeding of chrysanthemums", Euphytica, 15:156–162.

Dowrick, et al., 1966, "The induction of mutations in chrysanthemum using X–and gamma radiation", Euphytica, 15:204–210.

*Primary Examiner*—Howard J. Locker

*Attorney, Agent, or Firm*—Foley & Lardner

[57] ABSTRACT

A Chrysanthemum plant named White Blush particularly characterized by its flat capitulum form; daisy capitulum type; white ray floret color, with a cream-white color of the immature ray florets; diameter across face of capitulum of 114 to 121 mm when fully opened, when grown as a pinched disbudded pot mum; photoperiodic flowering response to short days of 49 to 55 days; plant height, with 20 to 22 long days after sticking unrooted cuttings, and with 1 to 2 applications of 2500 ppm B-9 SP, ranges from 20 to 30 cm when grown as a pinched pot mum with 4 cuttings in a 15 cm pot; branching pattern is semi-spreading, each plant having 3 to 5 laterals after pinch; and recommended as a disbudded pot mum.

1 Drawing Sheet

The present invention comprises a new and distinct cultivar of Chrysanthemum, botanically known as *Dendranthema grandiflora,* and referred to by the cultivar name White Blush.

White Blush, identified as 5661 (86-627D02), is a product of a mutation induction program. The new cultivar was discovered and selected by Cornelis P. VandenBerg on Jul. 23, 1990, in a controlled environment in Salinas, Calif., as one flowering plant within a flowering block established as rooted cuttings from stock plants which had been exposed as unrooted cuttings to an X-ray source of 2000 rads in Fort Myers, Fla., on Jan. 25, 1990. The irradiated parent cultivar was the cultivar identified as Blush, disclosed in U.S. Plant Pat. No. 7,985, and described as a disbud daisy pot mum with flat capitulum form; soft pink ray floret color; diameter across face of capitulum of 114 to 140 mm when fully opened, when grown as a pinched disbudded pot mum; flowering response period of 47 to 55 days after start of short days; plant height of 23 to 28 cm with 1 to 3 applicatins of 2500 ppm B-9 SP when grown as a pinched pot mum in a 15 cm pot; semi-spreading branching pattern, with 3 to 5 laterals after pinch; and recommended as a disbudded pot mum. The foregoing description of Blush has a somewhat wider range of measurements than the description of Blush in the noted plant patent. This is based on continued flowering trials of Blush after preparing and filing the patent application for Blush.

The irradiation program resulting in White Blush has as its primary objective the expansion of color ranges of the parent cultivar Blush. The irradiation program comprised irradiating cuttings of the parent cultivar at irradiation levels of 1500, 1750 and 2000 rads. A total of 1433 cuttings harvested from a total of 225 irradiated plants were planted on May 28, May 21 and May 14, 1990, respectively. Of these, 19 initial selections were made, which selections were then revegetated and reflowered. Three consecutive flowerings resulted in discarding 12 of the original 19 selections on Apr. 23, 1991. Seven selections were ratained and given PI (Possible Introduction) status. Continued flowering trials resulted in discarding 3 of the 7 remaining selections, and the decision to introduce 2 of the remaining selections in North America and Europe as White Blush and Coral Blush. Coral Blush is disclosed in pending application Ser. No. 08/296,446.

The remaining two selections were designated Pink Blush and Orange Blush. All four selections were introduced in Europe at the same time. Pink Blush and Orange Blush were introduced in the United States one year after introduction in Europe. Pink Blush is the subject of copending application Ser. No. 08/331,863 and Orange Blush is the subject of copending application Ser. No. 08/331,856.

The first act of asexual reproduction of White Blush was accomplished when vegetative cuttings were taken from the initial selection in Sep. 1990 in a controlled environment in Salinas, Calif., by technicians working under supervision of Cornelis P. VandenBerg.

Horticultural examination of controlled flowerings of successive plantings has shown that the unique combination of characteristics as herein disclosed for White Blush are firmly fixed and are retained through successive generations of asexual reproduction.

White Blush has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in comemrcial greenhouse practice.

The following traits have been repeatedly observed and are determined to be basic characteristics of White Blush, which, in combination, distinguish this Chrysanthemum as a new and distinct cultivar:

1. Flat capitulum form.
2. Daisy capitulum type.
3. White ray flroet color, with a cream-white color of the immature ray florets.
4. Diameter across face of capitulum of 114 to 121 mm when fully opened, when grown as a pinched disbudded pot mum.
5. Photoperiodic flowering response to short days of 49 to 55 days.
6. Plant height, with 20 to 22 long days after sticking unrooted cuttings and with 1 to 2 applications of 2500 ppm B-9 SP, ranges from 20 to 30 cm when grown as a pinched pot mum with 4 cuttings in a 15 cm pot.
7. Branching pattern is semi-spreading, each plant having 3 to 5 laterals after pinch.
8. Recommended as a disbudded pot mum.

The accompanying photographic drawing is a top perspective view of a potted mum of White Blush, with 4 cuttings in a 15 cm pot, with the colors being as nearly true as possible with illustrations of this type.

Of the commercial cultivars known to the inventor, the most similar in comparison to WHite Blush is the parent cultivar Blush. All traits of White Blush are similar to those of Blush, except for the ray floret color. The ray floret color of White Blush is white, while the ray floret color of Blush is soft pink. White Blush is distinguished from Coral Blush by ray floret color.

In the following description color references are made to The Royal Horticultural Society Colour Chart. The color values were determined on plant material grown as a pinched spray pot mum in Salinas, Calif. on Jul. 28, 1992.

Classification

*Botanical.*—*Dendranthema grandiflora* cv White Blush.

*Commercial.*—Flat daisy disbud pot mum.

INFLORESCENCE

A. Capitulum:
- *Form.*—Flat.
- *Type.*—Daisy.
- *Diameter across face.*—114 to 121 mm when fully opened.

Corolla of ray florets
- *Color (general tonality form a distance of three meters).*—White.
- *Color (upper surface).*—Mature 155D, immature 155A to 1D.
- *Color (under surface).*—155D.
- *Shape.*—Straight, pointed, slightly ribbed.

C. Corolla of disc florets:
- *Color (mature).*—7B.
- *Color (immature).*—144A to 144B.

D. Reproductive organs:
- *Androecium.*—Present on disc florets only; scant pollen.
- *Gynoecium.*—Present on both ray and disc florets.

PLANT

A. General appearance:
- *Height.*—20 to 30 cm when grown as a pinched pot mum with 20 to 22 long days prior to start of short days, with 1 to 2 applications of 2500 ppm B-9 SP.
- *Branching pattern.*—Semi-spreading, with 3 to 5 laterals after pinch.

B. Foliage:
- *Color (upper surface).*—147A.
- *Color (under surface).*—147B.
- *Shape and size.*—Moderately lobed and serrated; leaves are 75–85 mm long and 45–50 mm wide.

I claim:

1. A new and distinct Chrysanthemum plant named White Blush, as described and illustrated.

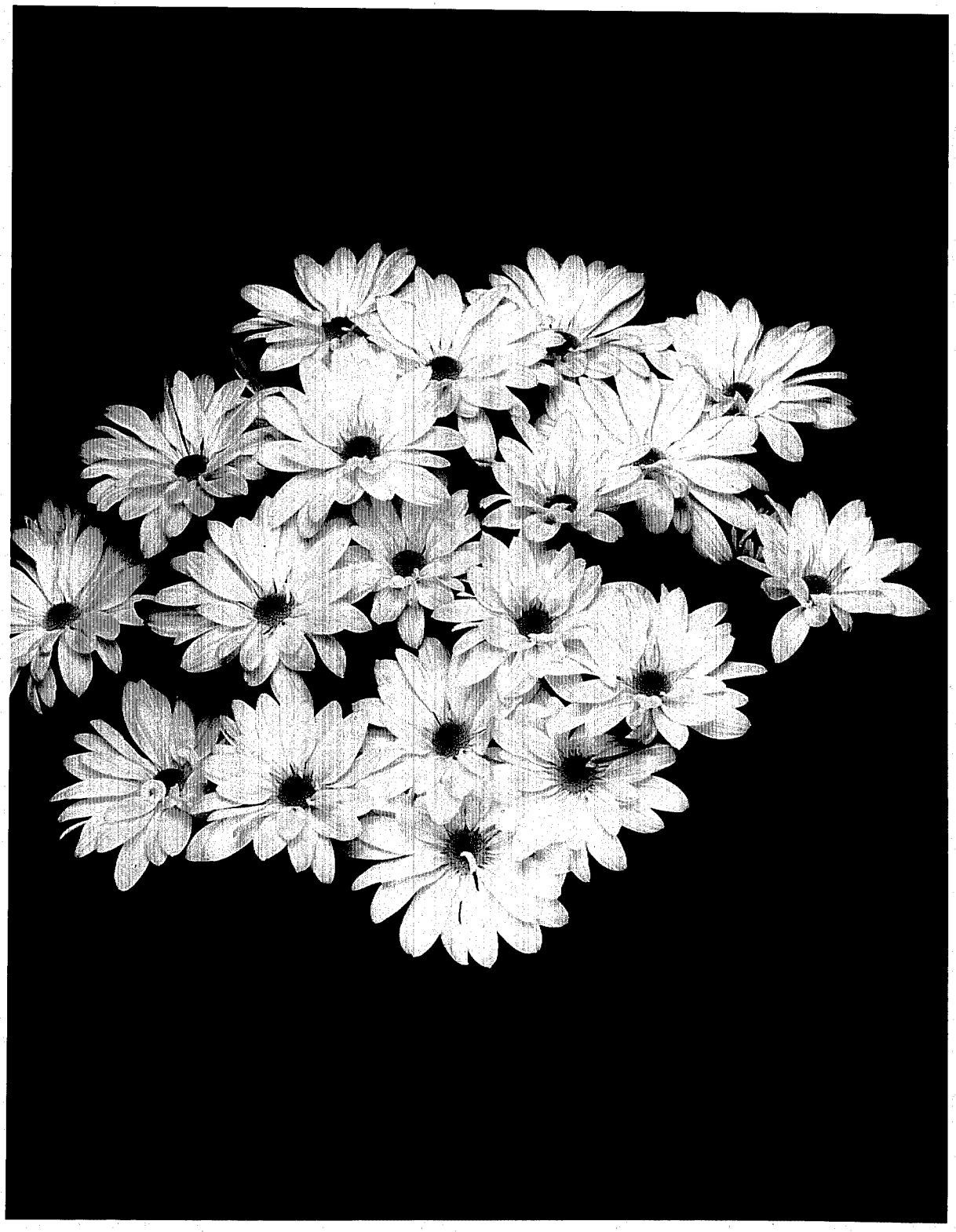

* * * * *